United States Patent [19]

Chu

[11] Patent Number: 4,822,939
[45] Date of Patent: Apr. 18, 1989

[54] PROCESS FOR THE CONVERSION OF LOWER ALIPHATIC OXYGENATES TO OLEFINS AND AROMATICS WITH GALLIUM CONTAINING ZSM-5 CATALYST

[75] Inventor: Cynthia T. W. Chu, Pennington, N.J.

[73] Assignee: Mobil Oil Corporation, New York, N.Y.

[21] Appl. No.: 163,587

[22] Filed: Mar. 3, 1988

Related U.S. Application Data

[63] Continuation-in-part of Ser. No. 884,842, Jul. 11, 1986, abandoned.

[51] Int. Cl.$^4$ .................. C07C 11/20; C07C 1/00
[52] U.S. Cl. ......................... 585/408; 585/640; 585/733
[58] Field of Search ............ 585/408, 640, 733

[56] References Cited

U.S. PATENT DOCUMENTS

| | | | |
|---|---|---|---|
| 3,979,472 | 9/1976 | Butter | 585/640 |
| 4,331,774 | 5/1982 | Boersma et al. | 585/469 |
| 4,361,715 | 11/1982 | Short et al. | 585/640 |
| 4,401,637 | 8/1983 | Marosi et al. | 324/329 |
| 4,483,835 | 11/1984 | Zones | 423/277 |
| 4,517,396 | 5/1985 | Hoek et al. | 585/415 |
| 4,550,217 | 10/1985 | Graziani et al. | 585/640 |
| 4,554,260 | 11/1985 | Pieters et al. | 502/61 |
| 4,582,949 | 4/1986 | Kieffer | 585/312 |

Primary Examiner—Curtis R. Davis
Attorney, Agent, or Firm—Alexander J. McKillop; Michael G. Gilman; L. G. Wise

[57] ABSTRACT

$C_2$–$C_5$ olefins and aromatics are prepared by catalytic conversion of lower aliphatic $C_1$–$C_4$ oxygenates in the presence of a medium pore gallium containing zeolite catalyst having a ZSM-5 framework at elevated conversion temperatures. The process favors production of valuable unsaturated hydrocarbons and aromatics with low paraffin output.

7 Claims, No Drawings

PROCESS FOR THE CONVERSION OF LOWER ALIPHATIC OXYGENATES TO OLEFINS AND AROMATICS WITH GALLIUM CONTAINING ZSM-5 CATALYST

REFERENCE TO RELATED APPLICATIONS

This application is a continuation-in-part of U.S. patent application Ser. No. 884,842 filed 11 July 1986, incorporated herein by reference, now abandoned.

BACKGROUND OF THE INVENTION

Recently, efforts to prepare olefins from methanol have become increasingly important. Methanol can be readily produced from coal, via coal gasification and the production of synthesis gas, with the aid of well-tried technology. If it were possible to convert methanol to lower olefins in an economical manner, the further processing methods which are conventional in the chemical industry today and employ coal as a raw material, could also be preserved. In the past few years, processes have, therefore, been developed with the object of preparing olefins from methanol, dimethyl ether or mixtures thereof.

U.S. Pat. Nos. 3,894,106 (Chang, et al.), 3,894,107 (Butter, et al.) and 3,907,915 (Chang, et al.), respectively, disclose the conversion of alcohols, ethers, carbonyls, or mixtures thereof to olefinic and aromatic hydrocarbons by contact with a catalyst comprising a crystalline aluminosilicate zeolite having a silica-to-alumina ratio of at least about 12 and a Constraint Index of about 1 to 12.

The conversion of methanol and dimethyl ether to olefinic and aromatic hydrocarbons is described in U.S. Pat. No. 3,911,041 (Kaeding, et al.).

German Laid-Open Application DOS No. 2,615,150 [from 4,503,281 (Hoelderich, et al.)]relates to a process for the preparation of olefins from a methanol feed using a ZSM-5 aluminosilicate zeolite.

U.S. Pat. No. 4,361,715 (short, et al.) relates to the catalytic conversion of lower molecular weight oxygenates to olefins over a bed of aluminosilicate zeolite catalyst. Gallium can be incorporated into the framework of the zeolite (Col. 1, line 51); however, the zeolite catalyst employed in the process of the Short, et al. patent does not have the ZSM-5 framework structure.

U.S. Pat. No. 4,401,637 (Marosi, et al.) discloses a process for preparing olefins from methanol over a catalyst bed of a modified crystalline isotactic zeolite comprising framework gallium and an organic amine of low basicity. The catalysts employed in the process of the Marosi, et al. patent differ from ZSM-5 type catalysts.

U.S. Pat. No. 4,582,949 (Kieffer), incorporated herein by reference, discloses a two-stage conversion process for the preparation of aromatic hydrocarbons from olefins over metallosilicate catalysts. A crystalline gallium silicate catalyst having a silicon dioxide to gallium trioxide ratio of between 25 and 250 and a specific X-ray powder diffraction pattern is employed in the second stage.

SUMMARY OF THE INVENTION

A new catalytic process has been discovered for the conversion of lower aliphatic $C_1$–$C_4$ oxygenates by a series of dehydration (or decarbonylation) and dehydrogenation reactions employing a medium pore acidic crystalline gallium-containing siliceous zeolite of ZSM-5 framework. It has been found that gallium containing ZSM-5 zeolites have superior catalytic activity in the production of $C_2$–$C_5$ olefins and aromatics, useful as intermediates in the preparation of gasoline/distillate or as valuable chemical feedstock. The process gives a much lower yield of less valuable $C_1$–$C_5$ paraffins than a similar process employing a standard aluminosilicate H-ZSM-5 catalyst.

DETAILED DESCRIPTION OF THE PREFERRED EMBODIMENT

The upgrading of lower molecular weight $C_1$–$C_4$ oxygenates, such as alcohols, ethers, ketones and their acetals, and carboxylates is achieved in an efficient manner by contacting the oxygenates under reaction conditions with a medium pore acidic crystalline gallium containing ZSM-5 type catalyst having at least a portion of zeolitic gallium in tetrahedral coordination therein to provide Bronsted acid sites.

In a preferred embodiment, the process comprises: maintaining a reaction zone containing a crystalline acidic gallium containing ZSM-5 catalyst; passing a feedstock comprising metahnol, dimethylether or mixtures thereof through the reaction zone at conditions of elevated temperature; and withdrawing a product rich in light olefins and aromatics. Preferably, the ratio of light olefins ($C_2$–$C_5$) to aromatic hydrocarbons is at least about 3:1. The amount of less desirable paraffinic hydrocarbons is reduced to a minimum by the process, producing less than 10 wt.% $C_1$–$C_5$ alkanes. At higher conversion temperatures, the ratio of aromatics to $C_1$–$C_5$ saturates is at least 2:1, and preferably at least 3:1.

Preferably, the process is conducted at conversion temperatures of about 500° C. (932° F.) to about 600° C.; and at conversion pressures up to about 3500 kPa. The weight hourly space velocity (WHSV) is normally about 1 to about 10.

The gallium zeolite catalyst can be prepared by various methods; for example: by a cocrystallization procedure, vapor phase treatment, or by employing an alkaline medium. A suitable starting material for the gallium treatment is a ZSM-5 zeolite having a high silica-to-alumina ratio of about 5,000 to 35,000 prior to gallium exchange. Such a zeolite material can be directly synthesized by known methods, or prepared from a zeolite having a low silica-to-alumina ratio by steaming, dealuminizing, or framework exchange (lattice substitution).

The prepared gallium containing zeolite, in a preferred embodiment, has the framework structure of ZSM-5 with Bronsted acid sites provided by tetrahedrally coordinated gallium in the framework structure. The zeolite is substantially free of tetrahedrally coordinated alumina with only minor or trace amounts of alumina in the zeolite lattice, wherein the amount of alumina in the zeolite is less than 0.5 wt.%. In a preferred embodiment the silica-to-alumina ratio of the gallium containing zeolite is at least about 26,000 to 1. The tetrahedral gallium of the framework may be indicated by ammonium exchange capacity and Nuclear Magnetic Resonance (NMR) signal. The tetrahedral gallium of the framework is present in an amount of at least 0.2 wt. %.

The Examples which follow illustrate the process according to the invention. Metric units and parts by weight are employed unless otherwise stated.

EXAMPLE 1

The gallium containing zeolite is synthesized by lattice substitution from ZSM-5 having a silica-to-alumina ratio of 26,000, which is calcined at 538° C. (1000° F.). A teflon bottle with 2g of the calcined ZSM-5 and 4g of $GaCl_3$ hydrated in 30 cc of $H_2O$ is sealed and heated up to 150° C. for 18 hours. The product is then washed and ion exchanged with 1N ammonium nitrate followed by calcination in air. This ZSM-5 catalyst contains 2.2% gallium.

EXAMPLE 2

A feedstock of methanol is reacted over a catalyst bed of gallium containing ZSM-5 zeolite prepared according to Example 1. The reaction is conducted at a temperature of 500° C. (932° F.) and a pressure of 101 kPa (1 atmosphere). The weight hourly space velocity (WHSV) of the methanol feed is about 1.

The results of the experiment are given in Column A of Table 1. At 98% conversion, the process produces a mixture of hydrocarbons consisting of 62 wt.% $C_2$–$C_5$ olefins, 20 wt.% aromatics, and only 6 wt.% $C_2$–$C_5$ light paraffins.

EXAMPLE 3

A feedstock of methanol is reacted over a catalyst bed of gallium containing ZSM-5 zeolite prepared according to Example 1. The reaction is conducted at a temperature of 370° C. (698° F.) and a pressure of 101 kPa (1 atmosphere). The weight hourly space velocity (WHSV) of the methanol feed is about 1.

The results of the experiment are given in Column B of Table 1. At 7% conversion, the process produces a mixture of hydrocarbons consisting of 81 wt.% $C_2$–$C_5$ olefins and 20 wt.% $C_1$–$C_5$ paraffins.

EXAMPLE 4

A feedstock of methanol is reacted over a catalyst bed of aluminosilicate ZSM-5 zeolite having a silica-to-alumina ratio of 1,670 and an acid-cracking (alpha) value of 5. The reaction is conducted at a temperature fo 500° C. (932° F.) and a pressure of 101 kPa (1 atmosphere). The weight hourly space velocity (WHSV) of the methanol feed is about 1.

The results of the experiment are given in Column C of Table 1.

EXAMPLE

A feedsotck of methanol is reacted over a catalyst bed of aluminosilicate ZSM-5 zeolite having a silica-to-alumina ratio of 500 and an acid-cracking (alpha) value of 12. The reaction is conducted at a temperature of 500° C. (932° F.) and a pressure of 101 kPa (1 atmosphere). The weight hourly space velocity (WHSV) of the methanol feed is about 1.

The results of the experiment are given in Column D of Table 1.

EXAMPLE 6

A feedstock of methanol is reacted over a catalyst bed of aluminosilicate ZSM-5 zeolite having a silica-to-alumina ratio of 70 and an acid-cracking (alpha) value of 150. The reaction is conducted at a temperature of 500° C. (932° F.) and a pressure of 101 kPa (1 atmosphere). The weight hourly space velocity (WHSV) of the methanol feed is about 1.

The results of the experiment are given in Column E of Table 1.

TABLE 1

| | Column | | | | |
|---|---|---|---|---|---|
| | A | B | C | D | E |
| Catalyst Type | Ga/ZSM-5 | Ga/ZSM-5 | ZSM-5 | ZSM-5 | ZSM-5 |
| $SiO_2/Al_2O_3$ Ratio | 26,000 | 26,000 | 1,670 | 500 | 70 |
| $C_1$–$C_5$ product | 5.89 | 19.48 | 6.59 | 10.91 | 37.56 |
| $C_2^=$–$C_5^=$ product | 62.04 | 80.82 | 79.81 | 71.67 | 38.01 |
| $C_6^+$ PON product | 11.54 | — | 5.21 | 4.34 | 1.7 |
| Aromatics product | 20.53 | — | 8.39 | 13.06 | 22.72 |
| % conversion | 98.14 | 7 | 99+ | 99+ | 99+ |

The results indicated in Table 1 illustrate the effectiveness of the inventive process for producing olefinic and aromatic hydrocarbons from oxygenate feed with a minimum formation of light paraffins.

While the invention has been described by reference to certain embodiments, there is no intent to limit the inventive concept except as set forth in the following claims.

I claim:

1. A process for the conversion of a feedstock containing lower aliphatic oxygenates to provide improved yields of aromatics and light olefins comprising: contacting the feedstock under reaction conditions of about 500° C. to about 650° C. and a weight hourly space velocity of about 1 to about 10 with a catalyst consisting essentially of gallium-containing zeolite having the structure of ZSM-5; said zeolite having a silica-to-alumina ratio of about 5,000 to 35,0000 prior to gallium exchange and having at least 0.2 weight percent of zeolite gallium in tetrahedral coordination therein; and recovering hydrocarbon product comprising a mixture of aromatic hydrocarbons, $C_2$–$C_5$ light olefins, and $C_1$–$C_5$ saturated hydrocarbons wherein the weight ratio of aromatics to saturates is at least 2 to 1, the ratio of light olefins to aromatics is at least 3:1, and wherein $C_1$–$C_5$ saturated hydrocarbons comprise less than 10 weight percent of the hydrocarbon product.

2. A process according to claim 1 wherein the aliphatic oxygenate feedstock comprises methanol, dimethyl ether, or mixtures thereof.

3. A process according to claim 1 wherein said gallium-containing zeolite consists essentially of ZSM-5 containing about 2.2 percent gallium.

4. A process according to claim 1 where at least 50 percent of said feedstock is converted to said hydrocarbon product.

5. A process according to claim 1 wherein said silica-to-alumina ratio of said gallium containing zeolite is at least about 26,000 to 1.

6. In a catalytic process for converting lower aliphatic oxygenate feedstock to aromatic rich olefin hydrocarbon product by contacting the feedstock at elevated temperature with siliceous medium pore, shape selective zeolitic catalyst under conversion conditions, the improvement wherein:

said zeolitic catalyst consists essentially of a gallium-containing crystalline metallosilicate substantially free of tetrahedrally coordinated alumina and wherein at least 0.2 weight percent of said gallium is present in tetrahedrally coordinated metallosilicate form;

said feedstock being substantially converted at a reaction temperature of about 500° C. to 600° C. and process pressure up to about 3,500 kPa; and wherein the hydrocarbon product contains a major amount of $C_2$–$C_5$ light olefins at a weight ratio of light olefins to aromatics greater than 3:1, less than 10% by weight $C_1$–$C_5$ alkanes, and aromatics are present in the hydrocarbon product at least three times the weight of $C_1$–$C_5$ alkanes.

7. A process according to claim 6 wherein the zeolitic catalyst comprises less than about 0.5 wt. % tetrahedrally coordinated alumina.

* * * * *